United States Patent [19]
Stoyka, Jr.

[11] Patent Number: 5,819,744
[45] Date of Patent: Oct. 13, 1998

[54] THERAPEUTIC MOUTHPIECE

[76] Inventor: Frank S. Stoyka, Jr., 1461 Sheridan Dr., Parma, Ohio 44134

[21] Appl. No.: 854,932

[22] Filed: May 13, 1997

[51] Int. Cl.⁶ ....................................................... A61C 5/14
[52] U.S. Cl. .......................................... 128/859; 128/861
[58] Field of Search ........................... 128/848, 859–862; 2/2; 602/902

[56] References Cited

U.S. PATENT DOCUMENTS

| | | | |
|---|---|---|---|
| 3,096,761 | 7/1963 | Moffett | 128/861 |
| 3,532,091 | 10/1970 | Lerman | 128/861 |
| 5,323,787 | 6/1994 | Pratt | 128/861 |
| 5,620,011 | 4/1997 | Flowers | 128/859 |

Primary Examiner—Michael A. Brown

[57] ABSTRACT

A new Therapeutic Mouthpiece for alleviating pain and reducing swelling within the mouth. The inventive device includes a pliable U-shaped member sized to fit within a mouth and adapted to generally conform in use to either the upper teeth or the lower teeth of the mouth, and a non-toxic cold temperature storage medium disposed within the U-shaped member. In use, a bottom wall portion of the U-shaped member abuts the occlusal surfaces of the teeth, an inner wall portion of the U-shaped member abuts the lingual surfaces of the teeth, and an outer wall portion of the U-shaped member abuts the buccal surfaces of the teeth and the adjacent gingival surface of the mouth. Accordingly, the cold temperature storage medium is optimally positioned to alleviate pain and reduce swelling within the mouth.

4 Claims, 2 Drawing Sheets

THERAPEUTIC MOUTHPIECE

BACKGROUND OF THE INVENTION

1. Field of the Invention

The present invention relates to oral treatment devices and more particularly pertains to a new Therapeutic Mouthpiece for alleviating pain and reducing swelling within the mouth.

2. Description of the Prior Art

The use of oral treatment devices is known in the prior art. More specifically, oral treatment devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art oral treatment devices include U.S. Pat. No. 4,983,122; U.S. Pat. No. 5,323,787; U.S. Pat. No. 4,138,814; U.S. Pat. No. 3,964,489; U.S. Pat. No. D246,671; and U.S. Pat. No. 4,240,436.

While these devices fulfill their respective, particular objectives and requirements, the aforementioned patents do not disclose a new Therapeutic Mouthpiece. The inventive device includes a pliable U-shaped member sized to fit within a mouth and adapted to generally conform in use to either the upper teeth or the lower teeth of the mouth, and a non-toxic cold temperature storage medium disposed within the U-shaped member.

In these respects, the Therapeutic Mouthpiece according to the present invention substantially departs from the conventional concepts and designs of the prior art, and in so doing provides an apparatus primarily developed for the purpose of alleviating pain and reducing swelling within the mouth.

SUMMARY OF THE INVENTION

In view of the foregoing disadvantages inherent in the known types of oral treatment devices now present in the prior art, the present invention provides a new Therapeutic Mouthpiece construction wherein the same can be utilized for alleviating pain and reducing swelling within the mouth.

The general purpose of the present invention, which will be described subsequently in greater detail, is to provide a new Therapeutic Mouthpiece apparatus and method which has many of the advantages of the oral treatment devices mentioned heretofore and many novel features that result in a new Therapeutic Mouthpiece which is not anticipated, rendered obvious, suggested, or even implied by any of the prior art oral treatment devices, either alone or in any combination thereof.

To attain this, the present invention generally comprises a pliable U-shaped member sized to fit within a mouth and adapted to generally conform in use to either the upper teeth or the lower teeth of the mouth, and a non-toxic cold temperature storage medium disposed within the U-shaped member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature an essence of the technical disclosure of the application. The abstract is neither intended to define the invention of the application, which is measured by the claims, nor is it intended to be limiting as to the scope of the invention in any way.

It is therefore an object of the present invention to provide a new Therapeutic Mouthpiece apparatus and method which has many of the advantages of the oral treatment devices mentioned heretofore and many novel features that result in a new Therapeutic Mouthpiece which is not anticipated, rendered obvious, suggested, or even implied by any of the prior art oral treatment devices, either alone or in any combination thereof.

It is another object of the present invention to provide a new Therapeutic Mouthpiece which may be easily and efficiently manufactured and marketed.

It is a further object of the present invention to provide a new Therapeutic Mouthpiece which is of a durable and reliable construction.

An even further object of the present invention is to provide a new Therapeutic Mouthpiece which is susceptible of a low cost of manufacture with regard to both materials and labor, and which accordingly is then susceptible of low prices of sale to the consuming public, thereby making such Therapeutic Mouthpiece economically available to the buying public.

Still yet another object of the present invention is to provide a new Therapeutic Mouthpiece which provides in the apparatuses and methods of the prior art some of the advantages thereof, while simultaneously overcoming some of the disadvantages normally associated therewith.

Still another object of the present invention is to provide a new Therapeutic Mouthpiece for alleviating pain and reducing swelling within the mouth.

Yet another object of the present invention is to provide a new Therapeutic Mouthpiece which includes a pliable U-shaped member sized to fit within a mouth and adapted to generally conform in use to either the upper teeth or the lower teeth of the mouth, and a non-toxic cold temperature storage medium disposed within the U-shaped member.

Still yet another object of the present invention is to provide a new Therapeutic Mouthpiece that could provide soothing relief for an individual who is experiencing discomfort resulting from dental surgery or trauma to the mouth. Typically, an individual experiencing such trauma or discomfort simply places an ice pack externally on their face adjacent the sore area or attempts to hold ice cubes within their mouth adjacent the sore area. Accordingly, the present invention replaces these standard methods for treating pain within the mouth by providing a more comfortable and effective means for providing cooling relief which, more specifically, would last longer than these standard methods and would not melt to become water within the mouth of the individual.

Even still another object of the present invention is to provide a new Therapeutic Mouthpiece that could also provide cooling relief for an individual, including individuals participating in sports and leisure activities as well as individuals working in warm environments. Thus, the present invention could provide these individuals with relief from the heat and a means for lowering their body temperature.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
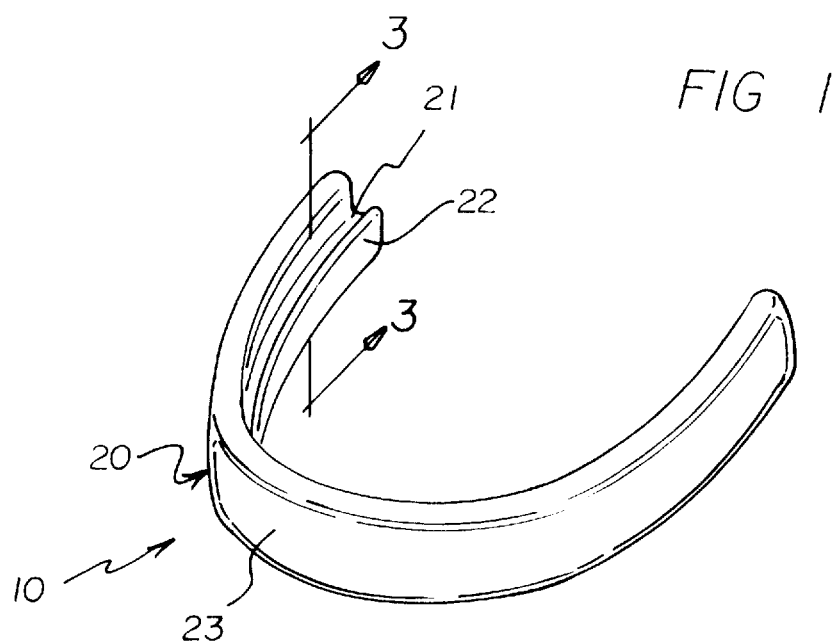
FIG. 1 is an illustration of a new Therapeutic Mouthpiece according to the present invention.
Figure 3:
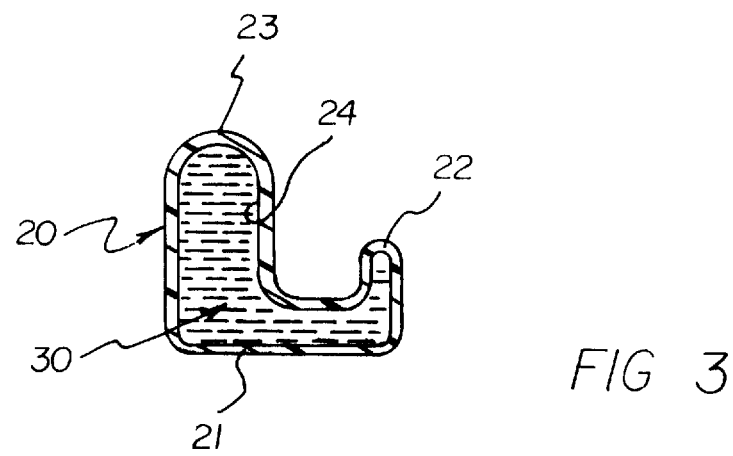
FIG. 3 is a cross sectional view taken along line 3—3 of FIG. 1.
Figure 2:
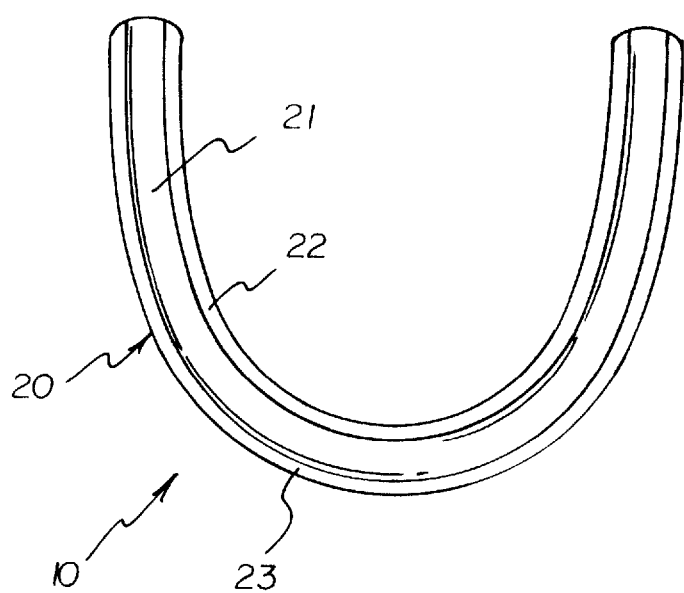
FIG. 2 is a top view thereof.

With reference now to the drawings, and in particular to FIGS. 1 through 3 thereof, a new Therapeutic Mouthpiece embodying the principles and concepts of the present invention and generally designated by the reference numeral 10 will be described.

As best illustrated in FIGS. 1 through 3, the Therapeutic Mouthpiece 10 comprises a pliable U-shaped member 20 sized to fit within a mouth and adapted to generally conform in use to either the upper teeth or the lower teeth of the mouth, and a non-toxic cold temperature storage medium 30 disposed within the U-shaped member 20.

The U-shaped member 20 includes a bottom wall portion 21, an inner wall portion 22, and an outer wall portion 23 all integrally joined to form a generally J-shaped cross-section. As such, the inner wall portion 22 is integrally joined to and perpendicularly extends from the bottom wall portion 21 along an inner periphery thereof. Furthermore, the outer wall portion 23 is integrally joined to and perpendicularly extends from the bottom wall portion 21 along an outer periphery thereof. As the U-shaped member 20 has a generally J-shaped cross-section, the outer wall portion 23 is of a height greater than that of the inner wall portion 22.

The U-shaped member 20 is configured to fit over either the upper teeth or the lower teeth of the mouth such that the bottom wall portion 21 abuts the occlusal surfaces of the teeth, the inner wall portion 22 abuts the lingual surfaces of the teeth, and the outer wall portion 23 abuts the buccal surfaces of the teeth and the adjacent gingival surface of the mouth when the Therapeutic Mouthpiece 10 is positioned within the mouth of a user.

As best illustrated in FIG. 3, the U-shaped member 20 has a substantially hollow interior 24. Moreover, the hollow interior 24 extends throughout the bottom wall portion 21, the inner wall portion 22, and the outer wall portion 23.

The non-toxic cold temperature storage medium 30 is disposed substantially throughout the hollow interior 24 of the U-shaped member 20. Since the hollow interior 24 of the U-shaped member 20 extends throughout the bottom wall portion 21, the inner wall portion 22, and the outer wall portion 23, the cold temperature storage medium 30 is correspondingly disposed throughout the bottom wall portion 21, the inner wall portion 22, and the outer wall portion 23 of the U-shaped member 20.

The cold temperature storage medium 30 is characterized by possessing the ability to be froze and thawed repeatedly. Typically, the cold temperature storage medium 30 is a gel-like compound characterized by the ability to remain cold for an extended period of time in ambient conditions. However, the cold temperature storage medium 30 may be water. In addition, the cold temperature storage medium 30 may comprise a chemical mixture that becomes cold when agitated.

It is contemplated that the Therapeutic Mouthpiece 10 be available in various sizes to accommodate mouths of various sizes. As such, sizes of the Therapeutic Mouthpiece 10 could include small, medium, large, and pediatric sizes. In addition, custom fit sizes could also be available.

In use, the U-shaped member 20 is positioned within the mouth of the user so as to fit over either the upper teeth or the lower teeth of the mouth. As such, the bottom wall portion 21 abuts the occlusal surfaces of the teeth, the inner wall portion 22 abuts the lingual surfaces of the teeth, and the outer wall portion 23 abuts the buccal surfaces of the teeth and the adjacent gingival surface of the mouth. When the U-shaped member 20 is positioned within the mouth of the user, the cold temperature storage medium 30 is optimally positioned so as to alleviate pain and reduce swelling within the mouth.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A therapeutic mouthpiece, comprising:

a pliable U-shaped member sized to fit within a mouth of a user and adapted to generally conform in use to at least one of upper teeth and lower teeth of the mouth of the user, said U-shaped member having a substantially hollow interior;

a non-toxic cold temperature storage medium disposed substantially throughout said hollow interior of said U-shaped member;

said cold temperature storage medium is a gel-like compound characterized by an ability to remain cold for an extended period of time in ambient conditions;

said cold temperature storage medium comprises a chemical mixture that becomes cold when agitated: and said U-shaped member has a generally J-shaped cross-section.

2. The therapeutic mouthpiece of claim 1, wherein said U-shaped member includes:

a bottom wall portion;

an integrally joined inner wall portion perpendicularly extending from said bottom wall portion along an inner periphery thereof;

an integrally joined outer wall portion perpendicularly extending from said bottom wall portion along an outer periphery thereof;

said outer wall portion being of a height greater than that of said inner wall portion;

said bottom wall portion abuts occlusal surfaces of the teeth;

said inner wall portion abuts lingual surfaces of the teeth;

said outer wall portion abuts buccal surfaces of the teeth and adjacent gingival surfaces of the mouth when said U-shaped member is positioned within the mouth of the user.

3. The therapeutic mouthpiece of claim 1, wherein said cold temperature storage medium is disposed throughout said bottom wall portion, said inner wall portion, and said outer wall portion of said U-shaped member.

4. A therapeutic mouthpiece, comprising:

a pliable U-shaped member insertable into a mouth of a user;

said U-shaped member having a substantially hollow interior and a generally J-shaped cross-section; and said U-shaped member comprising:

a bottom wall portion;

an integrally joined inner wall portion perpendicularly extending from said bottom wall portion along an inner periphery thereof;

an integrally joined outer wall portion perpendicularly extending from said bottom wall portion along an outer periphery thereof;

said outer wall portion having a height greater than that of said inner wall portion;

a non-toxic cold temperature storage medium disposed substantially throughout said hollow interior of said U-shaped member;

said cold temperature storage medium being disposed throughout said bottom wall portion, said inner wall portion, and said outer wall portion of said U-shaped member;

said cold temperature storage medium is a gel-like compound characterized by an ability to remain cold for an extended period of time in ambient conditions; and said cold temperature storage medium comprises a chemical mixture that becomes cold when agitated, said U-shaped member generally conforming in use to at least one of upper teeth and lower teeth of the mouth of the users;

said bottom wall portion abuts occlusal surfaces of the teeth;

said inner wall portion abuts lingual surfaces of the teeth;

said outer wall portion abuts buccal surfaces of the teeth and adjacent gingival surface of the mouth when said U-shaped member is positioned within the mouth of the user.

* * * * *